(12) United States Patent
Cerynik

(10) Patent No.: US 10,820,934 B2
(45) Date of Patent: Nov. 3, 2020

(54) SURGICAL GUIDEWIRE CENTERING DEVICE

(71) Applicant: Douglas Cerynik, Downingtown, PA (US)

(72) Inventor: Douglas Cerynik, Downingtown, PA (US)

(73) Assignee: Stabiliz Orthopaedics, LLC, Exton, PA (US)

( * ) Notice: Subject to any disclaimer, the term of this patent is extended or adjusted under 35 U.S.C. 154(b) by 115 days.

(21) Appl. No.: 15/290,385

(22) Filed: Oct. 11, 2016

(65) Prior Publication Data

US 2017/0100180 A1    Apr. 13, 2017

Related U.S. Application Data

(60) Provisional application No. 62/238,749, filed on Oct. 8, 2015.

(51) Int. Cl.
*A61B 17/88* (2006.01)
*A61B 17/72* (2006.01)

(52) U.S. Cl.
CPC .......... *A61B 17/8858* (2013.01); *A61B 17/72* (2013.01); *A61B 17/8897* (2013.01)

(58) Field of Classification Search
CPC .................. A61B 17/72–17/7291; A61B 17/88
See application file for complete search history.

(56) References Cited

U.S. PATENT DOCUMENTS

| 4,447,915 | A | 5/1984 | Weber | |
|---|---|---|---|---|
| 8,540,676 | B2 | 8/2013 | Geist | |
| 8,728,111 | B2 | 5/2014 | Geist | |
| 2005/0216007 | A1* | 9/2005 | Woll | A61B 17/7225 606/62 |
| 2008/0071223 | A1 | 3/2008 | Stauber | |
| 2008/0161805 | A1* | 7/2008 | Saravia | A61B 17/1725 606/60 |
| 2010/0145396 | A1 | 6/2010 | Thornes | |
| 2010/0274246 | A1 | 10/2010 | Beyar | |
| 2011/0190832 | A1 | 8/2011 | Taylor | |
| 2011/0257657 | A1* | 10/2011 | Turner | A61B 17/175 606/103 |
| 2012/0253410 | A1 | 10/2012 | Taylor et al. | |
| 2013/0245706 | A1 | 9/2013 | Euteneuer | |
| 2013/0267953 | A1 | 10/2013 | Brenzel | |
| 2014/0253410 | A1 | 9/2014 | DiNallo et al. | |

OTHER PUBLICATIONS

Mendenhall, S., "Orthopedic Network News," Mendenhall Associates, Ann Arbor, MI: s.n., vol. 22, No. 2, pp. 24 (2011).
(Continued)

*Primary Examiner* — Nicholas J Plionis
(74) *Attorney, Agent, or Firm* — Schott, P.C.

(57) ABSTRACT

A centering assembly for centering a surgical guidewire, includes a guidewire having an elongate body having a first end and a second end. The assembly further includes an expander located at the first end. The expander has a center point aligned with the elongate guidewire. An actuator is located at the second end. Actuation of the actuator moves the expander between a collapsed configuration and an expanded configuration.

5 Claims, 11 Drawing Sheets

(56) References Cited

OTHER PUBLICATIONS

Barrows, TH, "Degradable implant materials: a review of synthetic absorbable polymers and their applications," Clinical Materials, vol. 1, Issue 4, pp. 237-257 (1986).
Berry, M., "Bioresorbable Composite Materials for Orthopaedic Devices," Med Device Technol, vol. 19, No. 5, pp. 69-70 (2008).
Bottlang, M., et al., "Far cortical locking can reduce stiffness of locked plating constructs while retaining construct strength," J Bone Joint Surg Am, vol. 91, No. 8, pp. 1985-1994 (2009).
Chapiro, A., "Radiation chemistry of polymeric systems," London Interscience, p. 353 (1962).
Charlesby, A., "Radiation chemistry principles and applications," New York: VCH, p. 451 (1987).
Chia, NK, et al., "Controlled degradation of multilayered poly(lactide-co-glycolide) films using electron beam irradiation," J Biomed Mater Res A, vol. 84, Issue 4, pp. 980-987 (2008).
Claes, LE, et al., "Effects of mechanical factors on the fracture healing process," Clinical Orthopaedics and Related Research, vol. 355, pp. S132-S147 (1998).
Cross, III, W.W., and Brown, G.A., "Achieving stable fixation: Biomechanical designs for fracture healing," dated Jun. 2008, accessed at https://www.aaos.org/AAOSNow/2008/Jun/research/research4/, accessed on Jul. 6, 2018, pp. 1-3.
Duda, GN, et al., "Interfragmentary motion in tibial osteotomies stabilized with ring fixators," Clin Orthop Relat Res, vol. 396, pp. 163-172 (2002).
Egol, KA, et al., "Biomechanics of locked plates and screws," J Orthop Trauma, vol. 18, No. 8, pp. 488-493 (2004).
Frost & Sullivan, "US Trauma Fixation Markets," Palo Alto, CA: s.n., Section 4, pp. 11 (2007).
Ginde, RM, and Gupta, RK, "In vitro chemical degradation of poly(glycolic acid) pellets and fibers," J. Appl. Polym. Sci, vol. 33, Issue 7, p. 2411-2429 (1987).
Goodship, AE, and Kenwright, J., "The influence of induced micromovement upon the healing of experimental tibial fractures," The Journal of Bone and Joint Surgery, vols. 67-B, pp. 650-655 (Aug. 1985).
Henderson, C.E., et al., "Does Locked Plating of Periprosthetic Supracondylar Femur Fractures Promote Bone-Healing by Callus Formation? Two Cases with Opposite Outcomes," The Iowa Orthopaedic Journal, vol. 28, pp. 73-76 (2008).
Henderson, C.E., et al., "Locking Plates for Distal Femur Fractures: Is There a Problem With Fracture Healing?," J. Orthop. Trauma, Suppl, vol. 25, pp. S8-S14 (2011).
Ishikawa, M., "The effects of ultra-violet light and X-rays on aqueous solutions of poly-L-glutamic acid," Radiation and Environmental Biophysics, vol. 7, Issue 1, pp. 1-7 (1970).
Ishikawa, M., and Takakura, K., "Radiation effects of poly(L-glutamic acid) and poly(L-lysine) in the helix-coil transitional state," Radiation and Environmental Biophysics, vol. 13, Issue 2, pp. 115-123 (1976).
Kalfas, I.M., "Principles of bone healing," Neurosurg Focus, vol. 10, No. 4, pp. 1-4 (2001).
Kumar, GS, "Biodegradable Polymers: Prospects and Progress," Marcel Dekker Inc, New York, p. 36 (1982-83).
Loo, JSC, et al., "Degradation of poly(lactide-co-glycolide) (PLGA) and poly(L-lactide) (PLLA) by electron beam radiation," Biomaterials, vol. 26, Issue 12, pp. 1359-1367 (2005).
Loo, SCJ, et al., "Influence of electron-beam radiation on the hydrolytic degradation behaviour of poly(lactide-co-glycolide) (PLGA)," Biomaterials, vol. 26, No. 18, pp. 3809-3817 (2005).
Lungershausen, W., et al., "Locking plate osteosynthesis for fractures of the proximal humerus," Zentralbl Chir, vol. 128, No. 1, pp. 28-33 (2003).
Makadia, HK, and Siegel, S.J., "Poly Lactic-co-Glycolic Acid (PLGA) as Biodegradable Controlled Drug Delivery Carrier," Polymers, vol. 3, Issue 3, EISSN 2073-4360, pp. 1377-1397 (Aug. 2011).
Middleton, J.C., and Tipton, AJ, "Synthetic biodegradable polymers as orthopedic devices," Biomaterials, vol. 21, Issue 23, pp. 2335-2346 (2000).
Perren, S.M., et al., "Developments of compression plate techniques for internal fixation of fractures," Prag Surg, vol. 12, pp. 152-179 (1973).
Perren, SM., "Backgrounds of the technology of internal fixators," Injury, vol. 34, Suppl 2, pp. B1-B3 (2003).
Qui, L., "In vitro and in vivo degradation study on novel blends composed of polyphosphazene and polyester or polyanhydride," Polymer International, vol. 51, Issue 6, pp. 481-487 (2002).
Reich, G., "Ultrasound-induced degradation of PLA and PLGA during microsphere processing: influence of formulation variables," Eur J Pharm Biopharm, vol. 45, Issue 2, pp. 165-171 (1998).
Resch, H., et al., "Percutaneous fixation of three- and four-part fractures of the proximal humerus," J Bone Joint Surg Br, vol. 79, No. 2, pp. 295-300 (1997).
Rodan, GA, and Martin, TJ, "Role of osteoblasts in hormonal control of bone resorption: A hypothesis," Calcified Tissue International, vol. 33, No. 1, pp. 349-351 (1981).
Ronald, L., "General Principles of Internal Fixation," Medscape, cited Jun. 3, 2012, at accessed at http://emedicine.medscape.com/article/1269987-overview#aw2aab6b2, edited by Hasan, SA., accessed on Jul. 6, 2018, pp. 1-18.
Rubin, C.T., and Rubin, J.E., "Bone, Cartilage, and Heritable Connective Tissue Disorders," Edward D. Harris Jr (Ed.), Kelley's Textbook of Rheumatology, Seventh edition, Elsevier Saunders, vol. II, pp. 1449-1472 (2005).
Schatzker, J., "Changes in the AO/ASIF principles and methods," Injury, vol. 26, Supplement 2, pp. B51-B56 (1995).
Tan, SLE, and Balogh, ZJ., "Indications and limitations of locked plating," Injury, International Journal of the Care of the Injured, vol. 40, pp. 683-691 (2009).
Thanasas, C., et al., "Treatment of proximal humerus fractures with locking plates: a systematic review," J Shoulder Elbow Surg, vol. 18, No. 6, pp. 837-844 (2009).
Wu, XS, and Wang, N., "Synthesis, characterization, biodegradation, and drug delivery application of biodegradable lactic/glycolic acid polymers. Part II: Biodegradation," Journal of Biomaterials Science, Polymer Edition, vol. 12, Issue 1, pp. 21-34 (2001).
Kronenthal, R.L., et al., "Polymers in Medicine and Surgery," Polymer Science and Technology, Plenum Press, New York, pp. 119-137 (1975).
Schnabel, W., "Polymer Degradation—Principles and Practical Applications," Chapter 7, Hanser Pub Inc, Germany, pp. 179-215 (1981).

* cited by examiner

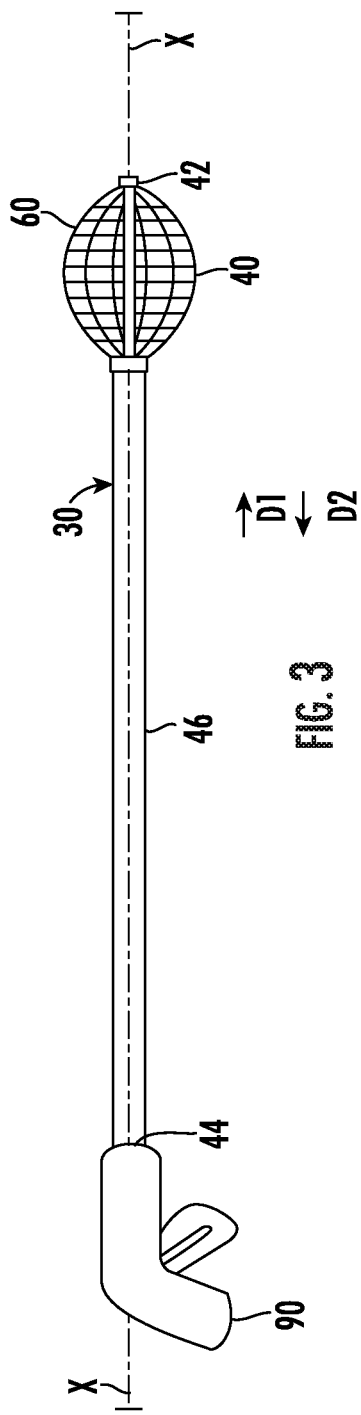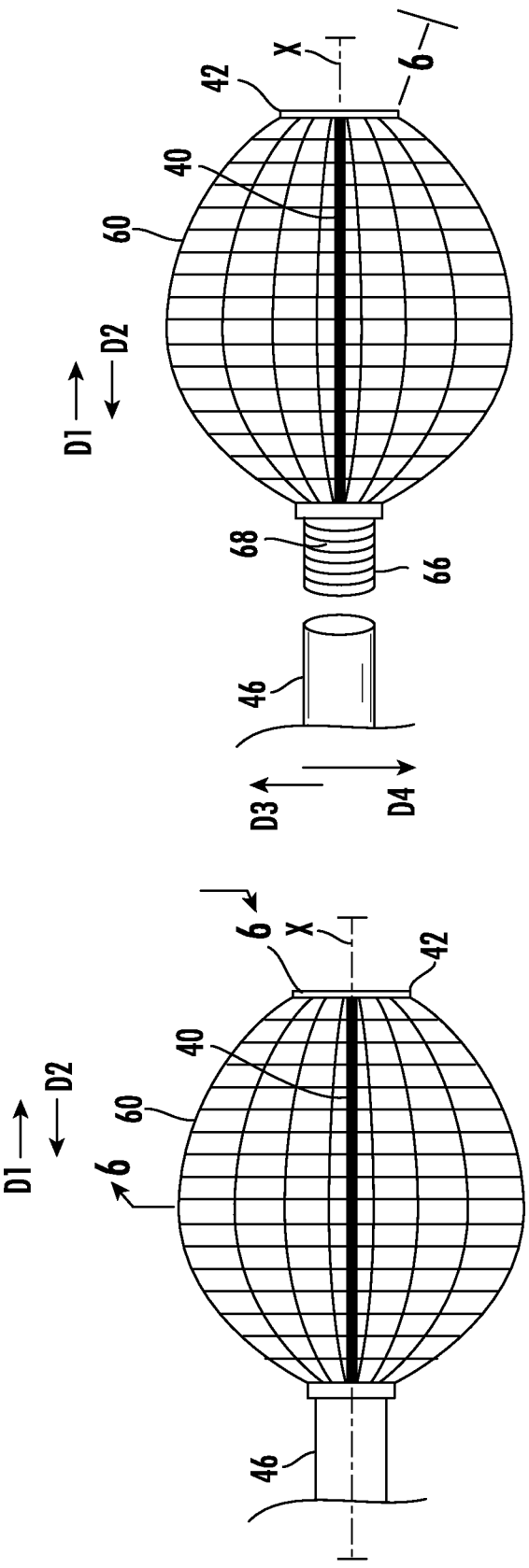
FIG. 3
FIG. 4
FIG. 5

SURGICAL GUIDEWIRE CENTERING DEVICE

CROSS REFERENCE TO RELATED APPLICATIONS

This application claims the benefit of U.S. Provisional Patent Application No. 62/238,749, filed Oct. 8, 2015 which is incorporated by reference as if fully set forth.

FIELD OF INVENTION

The invention relates generally to devices to assist in fixation of bone fractures. More specifically, the invention relates to devices for centering of an intramedullary wire during surgical fixation of bone fractures.

BACKGROUND

Intramedullary nailing is a procedure in which a bone fracture is fixed by driving an intramedullary nail into the medullary cavity of a bone. Such a procedure is commonly used to treat fractures of long bones, such as the femur, and is advantageous over other treatment procedures in that it minimizes surgical time and is less invasive. It can be challenging to position an intramedullary nail during such a procedure, and complications may arise were the nail is improperly positioned, such as anterior perforations of the femur due to anterior migration of the guidewire or nail during insertion. These complications are further elevated in the presence of osteoporosis and loss of adequate trabecular bone in the distal metaphysis. Elderly patients are particularly susceptible to these complications.

During an intramedullary nailing procedure, a surgical guidewire may be used for positioning of the intramedullary nail. The guidewire is inserted into the intramedullary cavity and may be over drilled, to create a canal within the medullary cavity for passage of the intramedullary nail. The intramedullary nail is then driven into position along the cavity. While use of a surgical guidewire helps to correctly position the nail, a need still exists for a device capable of ensuring correct positioning of the guidewire itself.

SUMMARY

The invention relates to a centering assembly for centering a surgical guidewire. The assembly includes a guidewire having an elongate body having a first end and a second end. The assembly further includes an expander located at the first end. The expander has a center point aligned with the elongate guidewire. An actuator is located at the second end. Actuation of the actuator moves the expander between a collapsed configuration and an expanded configuration.

The invention further relates to a centering device for centering a surgical guidewire. The device includes an elongate guidewire having a first end and a second end, and an expander located at the first end. The expander has a radial center point aligned with the elongate guidewire. The device further includes an actuator that compresses the expander in an axial direction to cause expansion of the expander in a radial direction.

The invention further relates to a method of centering a surgical guidewire during a surgical procedure. The method includes providing a centering assembly including an elongate guidewire having a first end and a second end, an expander located at the first end, the expander having a center point aligned with the elongate guidewire, and an actuator. The method further includes creating an incision for access to a surgical site, inserting the guidewire into the incision to position the expander at the surgical site, and actuating the actuator to expand the expander and center the guidewire.

The invention further relates to a method of centering a surgical guidewire during a surgical procedure. The method includes providing a centering assembly having an elongate guidewire having a first end and a second end, an expander configured for positioning at the first end, and an actuator. The method further includes creating an incision for access to a surgical site, inserting the guidewire into the incision and through the surgical site, and determining if the guidewire is centered within the surgical site. If the guidewire is not centered within the surgical site, the method further includes removing the guidewire from the surgical site, positioning the expander at the first end, reinserting the guidewire into the incision and through the surgical site, and actuating the actuator to expand the expander and center the guidewire.

A method of centering a surgical guidewire during a surgical procedure. The method includes providing a centering assembly including an elongate guidewire having a first end and a second end, an expander configured for sliding over the guidewire and positioning at the first end, and an actuator. The method further comprises creating an incision for access to a surgical site, inserting the guidewire into the incision and through the surgical site, determining if the guidewire is centered within the surgical site, and if the guidewire is not centered within the surgical site, sliding the expander over the guidewire to the first end, and actuating the actuator to expand the expander and center the guidewire.

BRIEF DESCRIPTION OF THE DRAWINGS

FIG. 3 is a perspective view of an embodiment of a guidewire centering assembly according to the invention, with the expander shown in an expanded configuration.

FIG. 4 is an enlarged detail of the assembly of FIG. 3, showing the expander in detail.

FIG. 5 is a partially exploded view of an expander according to the invention.

DETAILED DESCRIPTION OF THE PREFERRED EMBODIMENTS

Figure 1:
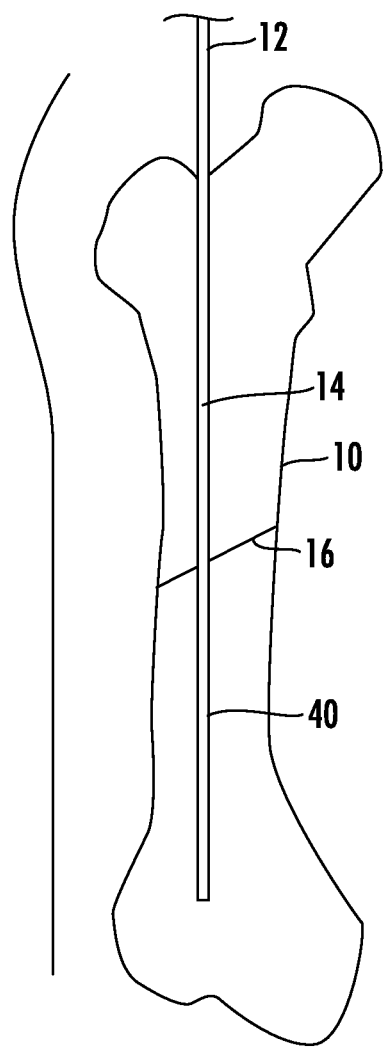
FIG. 1 is a cross sectional view of a femur during a stage of an intramedullary nailing procedure.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 2:
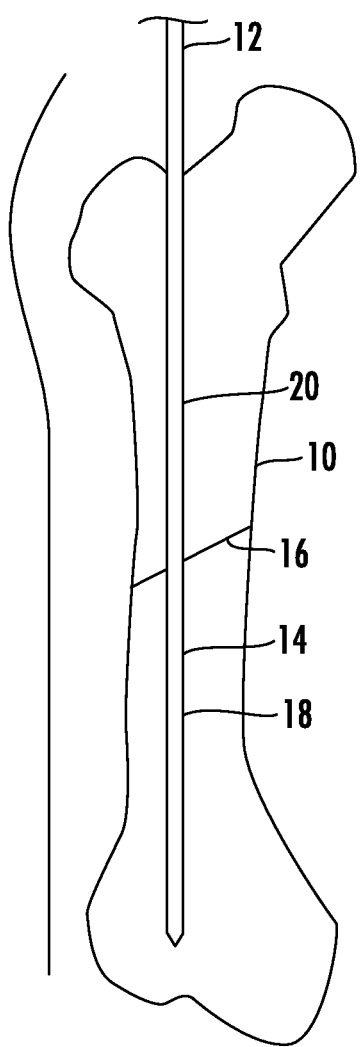
FIG. 2 is a cross sectional view of a femur during another stage of an intramedullary nailing procedure.

FIGS. 1 and 2 shows a human femur 10 during a conventional intramedullary nailing procedure. As shown, the femur 10 has a fracture 16 located near the longitudinal center thereof. During a fixing procedure, an incision 12 is made above the fracture 14, near the top of the femur 10. As shown in FIG. 1, a guidewire 40 is inserted into the incision 12 then driven into the femur 10, through the medullar canal 14, and through the fracture 14. The guidewire 40 is then over drilled to create a passage 18 for accommodating the intramedullary nail 20, which is then inserted through the passage 18 and through the fracture 16, as shown in FIG. 2.

Figure 6:
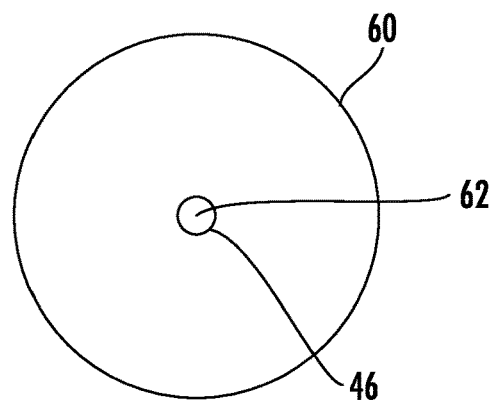
FIG. 6 is a cross sectional view taken along line 6-6 of FIG. 4.

FIG. 3 shows a first embodiment of an assembly 30 for centering a surgical guidewire according to the invention. As shown, the assembly 30 includes a surgical guidewire 40 having an elongate body including a first end 42 and a second end 44. The assembly 30 further includes an expander 60 located at the first end 42. The expander 60 can take on various shapes and configurations, as described in detail below, and when expanded has a radial center point 62 located in alignment with the guidewire 40, as shown in FIG. 6. The assembly 30 further includes an actuator 90 located at the second end 44. Actuation of the actuator 90 moves the expander 60 between a collapsed configuration, shown in FIG. 7, and an expanded configuration, shown in FIG. 4.

Referring to FIGS. 4 and 6, the expander 60 of the assembly of FIG. 3 is shown in an expanded configuration. As shown in FIG. 6, the expander 60 of this embodiment has a circular cross section when taken in a direction perpendicular to the axis X of the guidewire 40. The expander 60 may have a spherical body, as shown in FIG. 3, or may take on other shapes having a circular cross section, for example having a substantially spherical cross section that tapers as it extends outward in opposite axial directions. As shown in FIG. 6, the expander 60 has a radial center point 62 located in alignment with the guidewire 40, and in particular, located in alignment with the central axis X thereof, to facilitate centering of the guidewire 40 with respect to the centering assembly 30, and in turn within the surgical site, as described in detail below.

Referring again to FIG. 3, this embodiment of the assembly 30 further includes an outer sleeve 46 configured to slidably houses the guidewire 40. As shown, the sleeve 46 has an elongate tubular body, which, when fitted on the guidewire 40, extends the entire length of the guidewire 40, from first end 42 to second end 44. During a surgical procedure, the sleeve 46 is fitted on the guidewire and moved in an axial direction of the guidewire. Movement of the sleeve 46 on the guidewire 40 is controlled by the actuator 90, as described below. Moving of the sleeve 46 towards the first end 42 expands the expander 60, while moving of the sleeve 46 towards the second end 44 collapses the expander 60.

Figure 7:
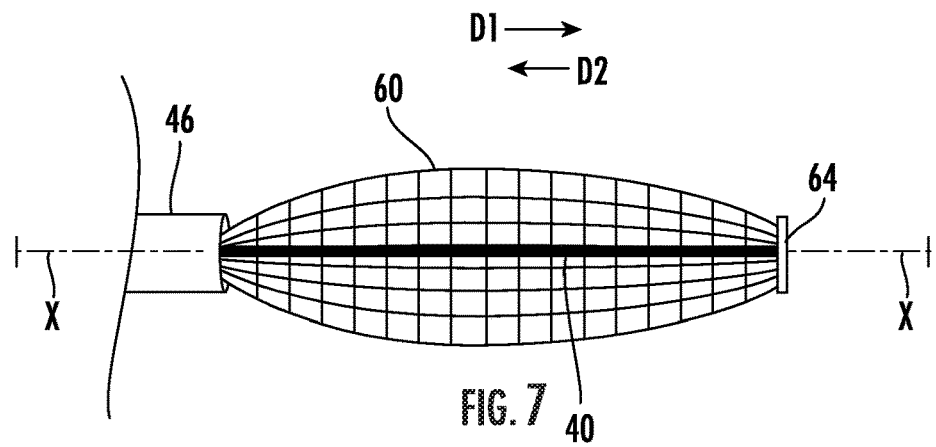
FIG. 7 is a perspective view of the expander of FIG. 4, with the expander in a collapsed configuration.

FIG. 7 shows the expander of this embodiment in a collapsed configuration. As shown, the sleeve 46 is fitted on the guidewire 40 at this stage, and the exits the sleeve 46 and passes through the expander 60, to an outer attachment tab 64 that affixes the first end 42 of the guidewire 40 with an outer end of the expander 60.

The expander 60 may be provided separately from the guidewire 40, and can configured for attachment thereto by way of attachment tab 64. The expander 60 of such embodiments could be configured to attach directly to the first end 42 of the guidewire, or could be configured to be slid over the length of the guidewire 40, until it reaches the first end 42. In some embodiments, the guidewire 40 may be configured for attachment to the expander by attachment tab 64, and in other embodiments, the attachment tab 64 could be configured to allow for attachment to a conventional guidewire 40. Likewise, in some embodiments, the sleeve 46, and guidewire 40 could be configured for affixing the sleeve 46 over the guidewire 40, while in other embodiments, a sleeve 46 configured for affixing over a conventional guidewire 40 could be provided.

Pushing of the sleeve 46 in direction D1, towards the first end 42, compresses the expander 60 in the direction of guidewire axis X, forcing it to expand radially outward, from the configuration of FIG. 7, to the configuration of FIG. 4. The expander 60 may be collapsed by drawing the sleeve 46 in direction D2, away from the first end 42, to lengthen the expander 60 in the direction of guidewire axis X, forcing it to retract radially inward, back to the configuration of FIG. 7.

The expander 60 may be formed of a mesh material, as shown in FIGS. 3 to 7, to allow for shifting of fibers as needed to facilitate expansion. In yet another embodiment, the expander is formed of an elastomeric material, and compression of the expander 60 in the axial direction causes outward expansion similarly to with the mesh embodiment of FIGS. 3 to 7. In yet another embodiment, the expander 60 could be formed of an elastomeric material, and the actuator 90 configured to supply gas to the expander, causing inflation in a balloon-like manner. The expander 60 may be affixed to the sleeve 46 in a various ways. As shown in FIG. 5, the expander 60 of this embodiment includes a threaded shaft 66 protruding from the end opposite the outer tab 64. The threaded shaft 66 may be tubular, to allow for passage of the guidewire 40 therethrough, and includes outer threads 68 configured to engage inner threads defined on an inner surface of the sleeve 46. In this way, the expander 60 and sleeve 46 are releasably attachable, and may, for example, be provided detached from each other and ready to be assembled with a suitable guidewire 40 when needed. In another embodiment, an expander 60 and sleeve 46 such as those shown in FIGS. 3-7 could be provided as a unitary structure. The expander 60 of FIG. 8 could optionally be configured to be unscrewed after insertion and centering of the guidewire 40, and to remain within the medullary cavity during and/or after the surgical procedure. In such an embodiment, the expander 60 could be formed of biodegradable materials and configured to dissolve within and be absorbed by the body.

In an embodiment, a threaded connection between the sleeve 46 and expander 60 such as that shown in FIG. 5, could be used to advance the sleeve 46 to expand the expander 60, as described above. In such an embodiment, the guidewire 46 is inserted into the passage 18 with the expander 60 in a collapsed configuration. In embodiments in which the sleeve 46 and expander 60 are provided as a unitary structure, they could be engaged by such a threaded connection, and at the time of insertion the threaded connection between the sleeve 46 and the expander 60 could be only partially engaged. In another embodiment, the expander 60 may be formed integrally with the guidewire 40, for example, by affixing the expander 60 to the guidewire 40 via connections located at the outer tab 64 and guidewire 60. Still in another embodiment, the sleeve 46 and expander 60 could be formed as an integral structure, for example by way of a threaded connection as described above, and the guidewire 40 and expander 60 could be affixed, for example by way of a connection between guidewire 60 and outer tab 64, the entire assembly 30 being formed as a unitary structure. In yet another embodiment, each the expander 60, guidewire 40 and sleeve 46 could each be provided individually.

The sleeve 46 is advanced until it engages the expander 60, and then rotated with respect to the shaft 66, which may be achieved by using a suitable actuator known in the art and capable or rotating the sleeve. Rotating the sleeve 46 in a first direction D3 engages the threads, driving the sleeve 46 in direction D1 towards the first end 42 of the guidewire 40, to cause expansion of the expander 60 in the manner to that described above. Rotating the sleeve 46 in a second direction D4 disengages the threads, withdrawing the sleeve 46 in direction D2, until the shaft 66 and sleeve 46 fully disengage, releasing the expander 60 from the sleeve 46. In an embodiment, the expander 60 may be configured to collapse at this point, due to withdrawal of the sleeve 46. In another embodiment, the expander 60 may be configured to stay in an expanded configuration, which could be achieved, for example, by forming the expander 60 of a malleable material that allows for expansion when pressure is applied by the shaft 66, but retains its shape upon removal of such pressure. Such an embodiment allows for removal of the sleeve 46, while maintaining placement of the guidewire 40 and expander 60, keeping the guidewire 40 centered prior to drilling and nail insertion.

Figure 8:
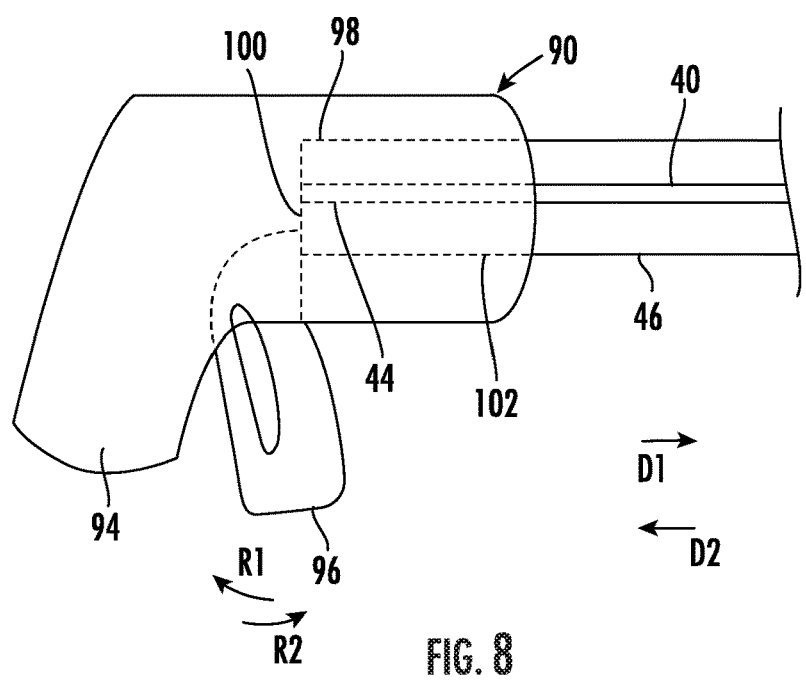
FIG. 8 is an enlarged detail of the assembly of FIG. 3, showing the actuator in detail.

Various types of actuators could be employed with an assembly 30 according to the invention. FIG. 8 shows one embodiment of an actuator 90. The actuator 90 of this embodiment is configured to move the sleeve 46 in opposite directions D1, D2, in order to expand and contract the expander, as described above. As shown, the actuator 90 includes a body 92 having a grip 94 and an attachment portion 98 configured for releasable attachment of the sleeve 46 and guidewire 40. A trigger 96 is pivotally affixed to the body 92 and includes a tab 100 that extends into a groove 102 defined in the body, the groove 102 being in communication with the attachment portion 98. As shown, tab 100 is in contact with the sleeve 46. The trigger 96 pivots with respect to the body 92 to move the tab 100 within the groove. Pivoting the trigger 96 in a first direction R1 causes the tab 100 to push the sleeve 46 in direction D1 towards the first end 42 of the guidewire 40, resulting in expansion of the expander 60, and pivoting the trigger 96 in a second direction R2, opposite the first direction, causes the tab 100 to draw the sleeve 46 in direction D2 towards the second end 44 of the guidewire 40, resulting in collapsing of the expander 60. Other types of actuators known in the art could be employed as well. In other embodiments, in which the expander 60 is engaged with the sleeve 46 by way of a threaded connection such as that shown in FIG. 5, an actuator capable of rotating the sleeve 46 could be employed.

Figure 9:
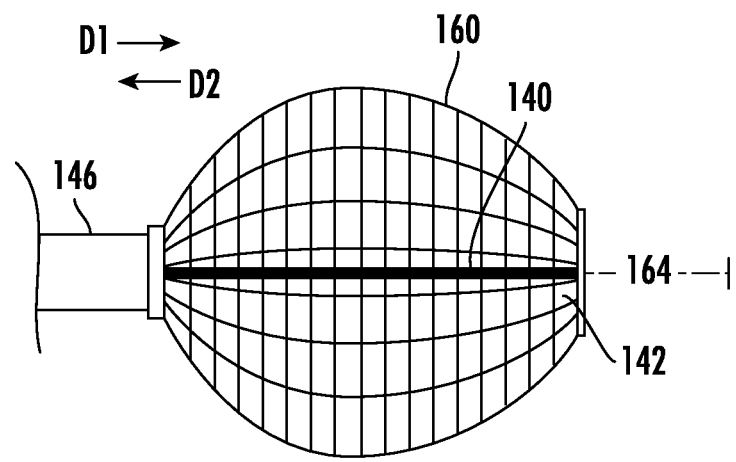
FIG. 9 is a perspective view of another embodiment of an expander according to the invention, shown in an expanded configuration.
Figure 10:
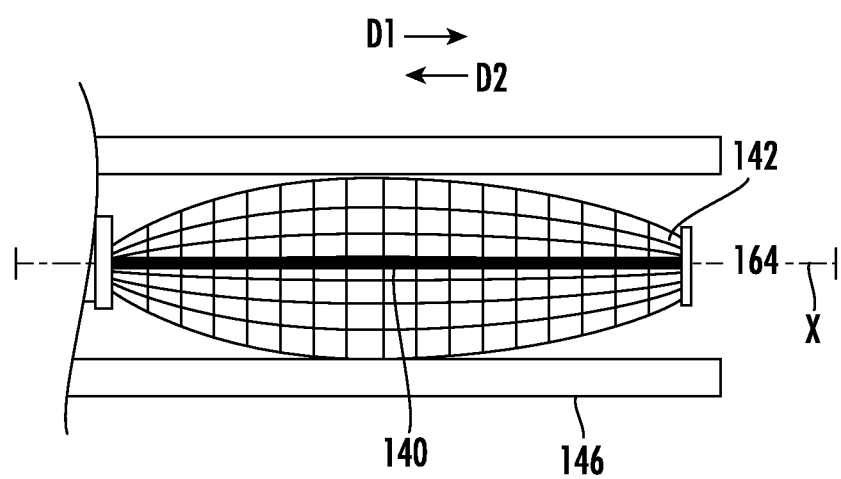
FIG. 10 is a longitudinal cross sectional view of the expander of FIG. 9, in a collapsed configuration.

Another embodiment of an expander 160 according to the invention is shown in FIGS. 9 and 10. This embodiment of the expander 160 is similar to that shown in FIGS. 3 to 7 and described above, and only the differences will be described in detail, with analogous structures designated using the same reference number, increased by 100. In this embodiment, the expander 160 is biased towards the expanded configuration, which may be achieved, for example, by forming the expander of a resilient material. The sleeve 146 of this embodiment is configured to slide over the expander 160, such that the expander 160 is housed within the sleeve 146, between the sleeve 146 and the guidewire 40 to retain the expander in the collapsed configuration, as shown in FIG. 10. In order to expand the expander of this embodiment, the sleeve 146 is drawn in direction D2, towards the second end 44 of the guidewire 140, to release the expander 160, allowing it to expand radially outward to the configuration shown in FIG. 9. Sliding of the sleeve 146 may be achieved using a suitable actuator, such as that shown in FIG. 8.

Figure 11:
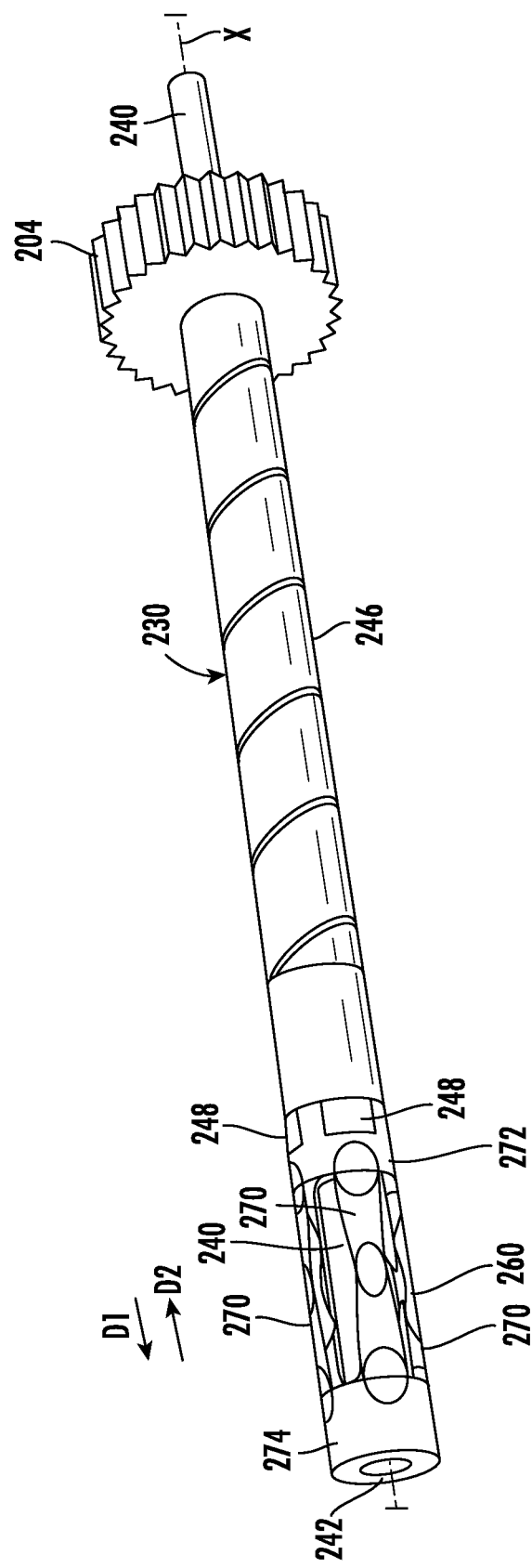
FIG. 11 is a perspective view of another embodiment of a guidewire centering assembly according to the invention, with the expander shown in a collapsed configuration.
Figure 12:
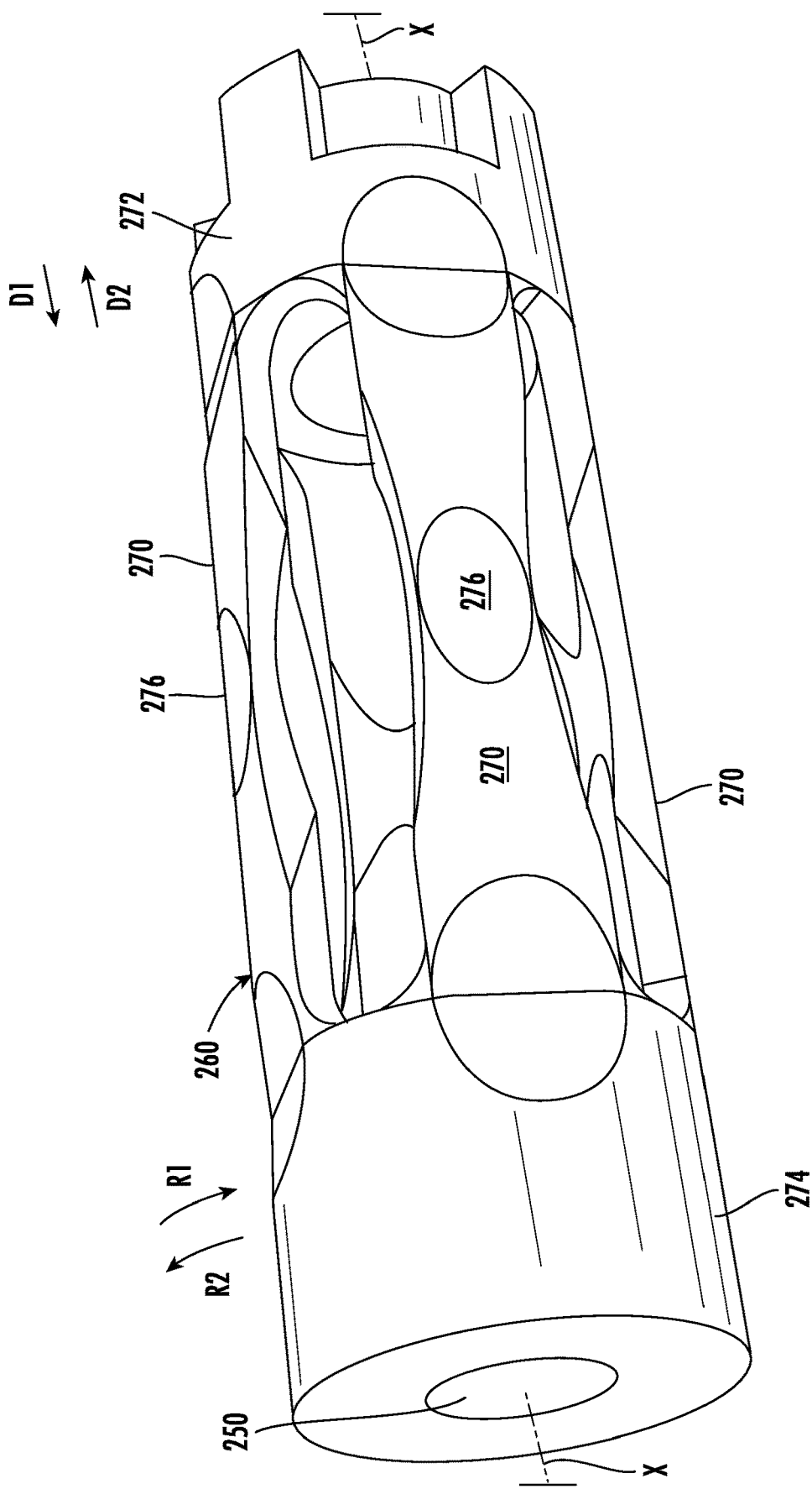
FIG. 12 is an enlarged detail of the assembly of FIG. 11, showing the expander in detail.
Figure 13:
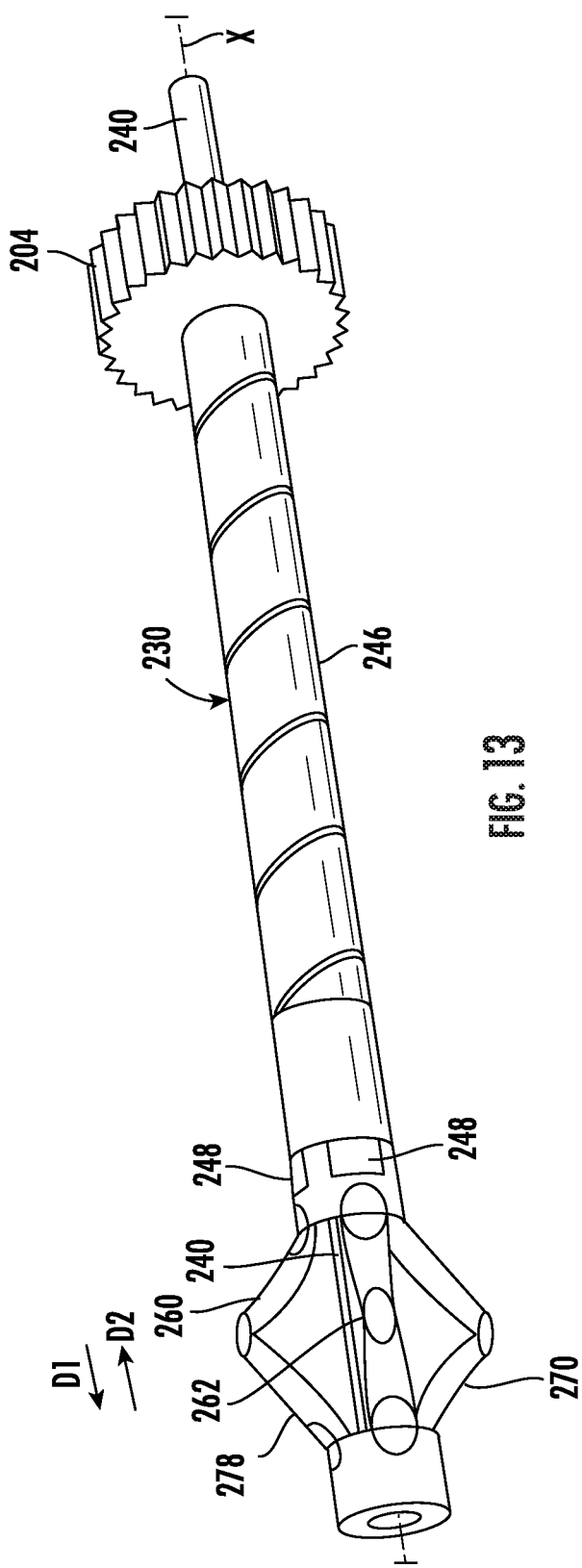
FIG. 13 is a perspective view of the assembly of FIG. 11, with the expander shown in an expanded configuration.

FIGS. 11 to 13 show another embodiment of an expander 260 according to the invention. This embodiment is similar to those of FIGS. 3 to 7 and only the differences will be described in detail, with analogous structures designated using the same reference numbers, increased by 200. This embodiment of the expander 260 has a non-circular cross section when in the expanded configuration. In particular, this version of the expander 260 is formed of a plurality of ribs 270, extending between an inner collar 272 and an outer collar 274. This embodiment of the expander 260 includes four ribs 270, and takes on a square cross sectional shape, but it should be understood that the number of ribs 270 could be varied. The expander 260, like that of FIGS. 3 to 7, has a radial center point 262 in alignment with the guidewire 240. Ribs 270 may be made of a flexible material, so as to allow for bending during expansion, or, as shown in FIG. 11, include hinge points 276 to allow for bending, the hinge points 276 of the embodiment shown being located at about the longitudinal center of each rib 270.

Inner collar 272 and outer collar 274 are each slidably seated on the guidewire 240 in the embodiment shown in FIGS. 11 to 13. In the embodiment shown, inner collar 272 includes a plurality of recesses 272 extending inward from an outer axial edge thereof, and a plurality of complimentary tabs 248 extend from an end of sleeve 246, to retain the sleeve 246 in a fixed rotational position with respect to the expander 260. Sleeve 246 has an elongate tubular body, which, when fitted on the guidewire 240, extends the entire length of the guidewire 240, from first end 242 to second end 244. Sliding of the sleeve 246 on the guidewire 240 is controlled by an actuator, which may be configured similarly to the actuator 290 shown in FIG. 8. The actuator could take on other configurations as well, and the embodiment of FIGS. 11 to 13 includes a gear 204 affixed to the sleeve 240 near the second end 244 of the guidewire 240, the gear 204 being adapted to engage a suitable actuator in a known manner for driving the sleeve 246 along the guidewire 240. Sliding of the sleeve 246 towards the first end 242 expands the expander 260, while sliding of the sleeve 46 towards the second end 244 collapses the expander 260.

FIGS. 11 and 12 show the expander 260 of this embodiment in a collapsed configuration. As shown, the sleeve 246 is fitted on the guidewire 240 at this stage, such that the guidewire 240 passes through the expander 260, through inner collar 272 and outer collar 274. Each of the ribs 270 is fully extended in the axial direction of the assembly 230. Pushing of the sleeve 246 in direction D1, towards the first end 242 compresses the expander 260 by forcing inner collar 272 towards first end 242, which results in inward pivoting of ribs 270 about their respective hinge points 276, which in turn draws outer collar 274 towards the second end 244. During this process, the inner collar 272 and outer collar 274 move towards each other, and expander 260 expands in a radially outward direction, to the configuration of FIG. 13. The expander 260 may be collapsed by drawing the sleeve 246 in direction D2, away from the first end 242, to lengthen the expander 260 by allowing the inner collar 272 and outer collar 274 to move apart, and the ribs 270 to pivot to the configuration of FIGS. 11 and 12.

Figure 23:
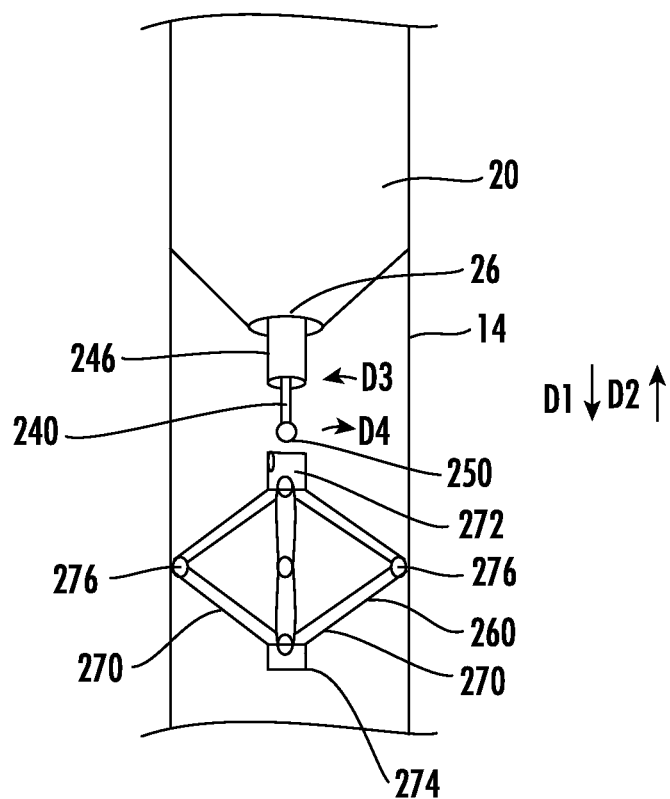
FIG. 23 is an enlarged detail showing a stage of another method of conducting an intramedullary nailing procedure.

In another embodiment, an expander 260 and guidewire 240 such as those shown in FIGS. 11 to 13 could be provided as an assembly, with the guidewire 240 adapted to retain the expander 260 thereon. In one exemplary embodiment, the outer collar 274 includes inner threads, and the guidewire 240 includes a threaded engagement rod 250 (FIG. 12) that extends through the section of guidewire 240 beneath the outer collar 274, such that rotation of the expander 260 drives the outer collar 274 in an axial direction. In such an embodiment, a suitable actuator could engage and rotate the sleeve 246, for example, via the gear 204 in the illustrated embodiment. Due to the engagement between tabs 248 and recesses 278, this rotation of the sleeve 248 drives rotation of the expander 260. Rotation of the sleeve 246 in a first direction R1 moves the outer collar 274 in direction D2, towards the second end 244 expands the expander 260, drawing inner collar 272 and outer collar 274 towards each other by way of pivoting of the ribs 270 as they expand, while rotation of the sleeve 246 in a second direction R2 moves the outer collar 274 in direction D1, towards the first end 242, compresses the expander 260, pushing the inner collar 272 and outer collar 274 away from each other. Optionally, such a threaded outer collar 274 could be used as a release mechanism for releasably affixing the expander 260 over the guidewire. In such an embodiment, rotation of the sleeve 246 in direction R2 as described above could be continued, moving outer collar 274 in direction D1 until it becomes fully disengaged from the guidewire 240, at which point the guidewire 240 can be withdrawn from the expander 230. In an embodiment, the ribs expander 260 could be configured to stay permanently in an expanded state, once the expanded state is reached. Such an expander 260 could be configured to be left within the body after withdrawal of the guidewire 240, for example as shown in FIG. 23, and could be further left within the body after the procedure, optionally being formed of a biodegradable material that allows for absorption by the body.

In another embodiment, a threaded connection between the outer collar 274 and guidewire 240 such as that described above could be employed, but the guidewire 240 configured to rotate with respect to the sleeve 246 and expander 260, such rotation being driven by a suitable tool capable of rotating the guidewire 240.

Figure 14:
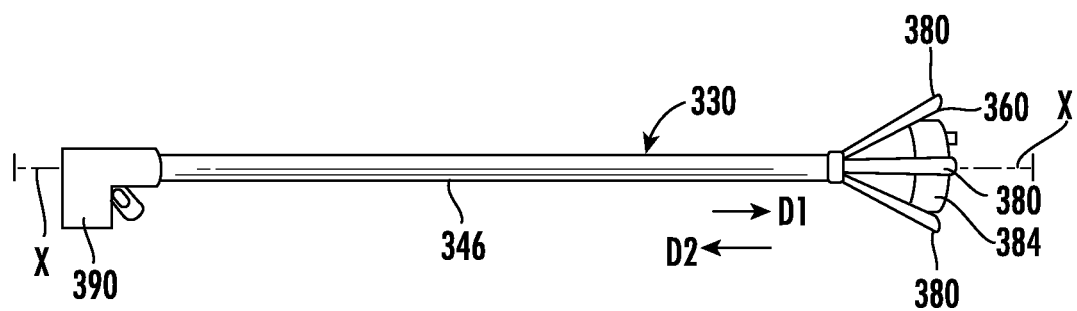
FIG. 14 is a perspective view of another embodiment of a guidewire centering assembly according to the invention, with the expander in an expanded configuration.
Figure 15:
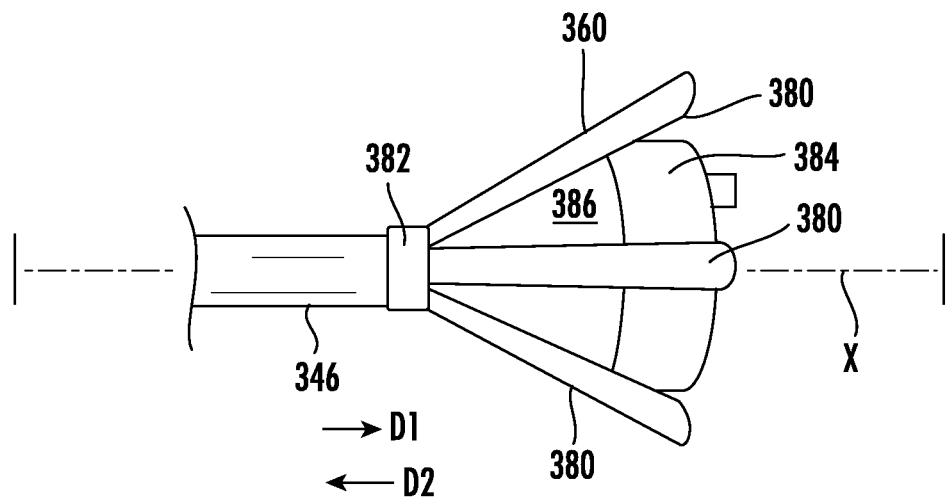
FIG. 15 is an enlarged detail of the assembly of FIG. 14, showing the expander in detail.
Figure 16:
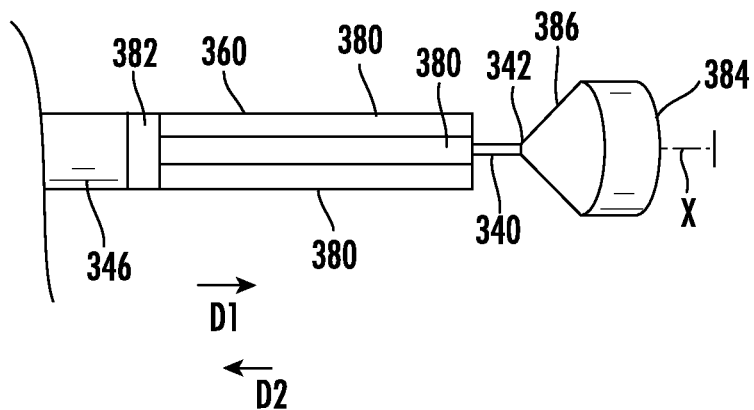
FIG. 16 is shows the expander of FIG. 15 in a collapsed configuration.

FIGS. 14 to 16 show another embodiment of an expander 360 according to the invention. This embodiment is similar to that shown in FIGS. 3 to 7, and only the differences will be described in detail, with the same reference number used to designate analogous structures, increased by 300. As shown, the expander 360 of this embodiment includes a plurality of elongated prongs 380 pivotally affixed about a central body 382. The body 382 defines a passage, with the guidewire 370 passing through the passage 382, allowing the expander 360 to slide along the axial length of the guidewire 340. The assembly 330 of this embodiment further includes a stop 384 located at the first end 342 of guidewire 340. Stop 384 includes at least one tapered surface 386 facing the second end 344. The at least one tapered surface 386 can include single conical surface 384, as in the embodiment shown, or may include a plurality of substantially planar angled surfaces, each corresponding to and being positioned in alignment with one of the prongs.

Figure 17:
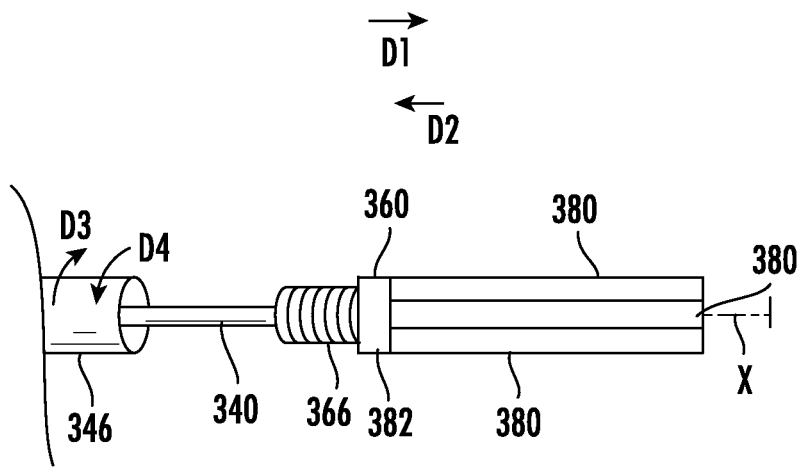
FIG. 17 is a partially exploded view of the expander of FIG. 16.

In order to expand the expander 360, the sleeve 346 is driven in direction D1, towards the first end 342. This may be achieved using an actuator, such as that shown in FIG. 8 and described above, or another actuator known in the art. In another embodiment, the expander 360 may include a threaded shaft 366, as shown in FIG. 17, the threaded shaft 366 configured to engage inner threads formed on an inner surface of the sleeve 346, such that rotation of the sleeve 346 moves the expander 360 in direction D1.

The expander 360 is moved in direction D1 until it reaches the stop 374, at which point each of the prongs 380 contacts the tapered surface 386 of the stop 384. The body 382 of expander continues to advance, while the prongs 380 are pivoted radially outward by way of their contact with tapered surface 386, until the body 382 reaches the stop 384 to prevent further movement of the expander 360, at which point each of the prongs 380 is in the fully expanded position shown in FIGS. 14 and 15. The prongs 380 may optionally be biased towards the closed position, for example by being spring loaded, such that retracting the sleeve 346 will result in the prongs 380 pivoting back to the positions shown in FIG. 16.

A method of centering a guidewire using an assembly according to the invention is shown in FIGS. 18 to 23. The assembly of FIGS. 11 to 13 is shown and described in detail, but any of the assemblies described herein could be used in a similar procedure.

Figure 18:
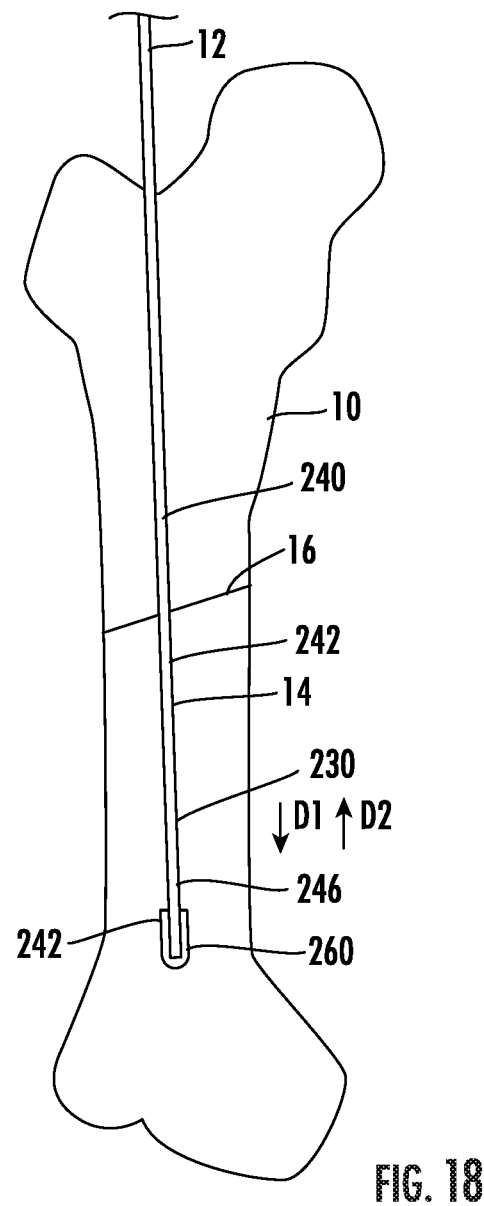
FIG. 18 shows a stage of an intramedullary nailing procedure.
Figure 19:
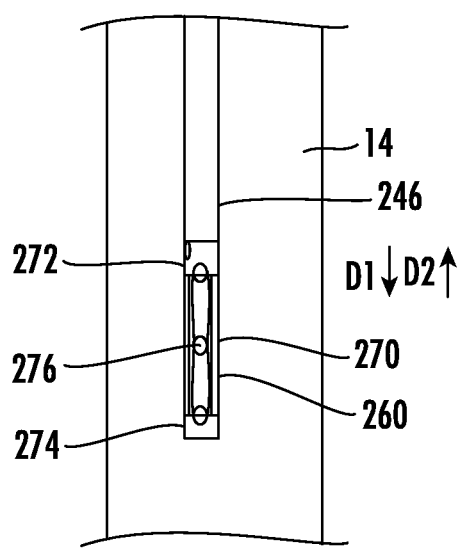
FIG. 19 is an enlarged detail of FIG. 18, showing the expander in detail.

Referring first to FIG. 18, a first stage of in intramedullary nailing procedure is shown. As shown, an incision 12 is made above the patient's femur 10 and a guidewire 240 inserted through the incision and into the medullary channel 14 of the femur 10. The guidewire 240 passes through the fracture 16. The expander 260 is in a collapsed state at this stage, as shown in FIG. 19, and is located at the first end 242 of the guidewire 240. In an embodiment, the guidewire 240 could initially be inserted without the expander 260, for example as shown in FIG. 1, subsequently removed if it is determined that the guidewire 240 is not centered, and then assembled with the expander 260 positioned at the first end 242, and reinserted as shown in FIG. 18. In another embodiment, the guidewire 240 could be inserted with the expander 260 affixed thereon, as either a permanent or unitary structure, and then a determination made as to whether the guidewire 240 is centered, the expander 260 only being actuated if the guidewire 240 is not centered. In yet another embodiment, the guidewire 240 and expander 260 could be provided as separate components, and the guidewire 240 could initially be inserted without the expander 260, in the manner shown in FIG. 1. A determination could then be made as to whether the guidewire 240 is centered, and if the guidewire 240 is not centered, the expander 260 could be threaded onto the guidewire 240 while the guidewire 240 is located within the body. In still another embodiment, the expander 260 and sleeve 246 could be provided as a unitary structure, as described above, and could be together threaded onto the guidewire 240 at this point. Where the sleeve 246 and expander are provided separately, the sleeve 246 is then placed over the guidewire 240 and advanced in direction D1, using an actuator 290 (FIG. 8), until it comes in contact with the expander 260, as shown in FIG. 19. Further advancing of the sleeve 246 results in expansion of the expander 260 in the manner described above, as shown in FIG. 20. In this particular embodiment, the inner collar 272 moves in direction D1 by force of the sleeve 246, resulting in pivoting of the ribs 270 about hinge points 276, expanding the expander 260 in a radially outward direction. At this time outer collar 274 is also drawn towards inner collar 272. Where expanders according to other embodiments of the invention are employed, the expander would expand as described with respect to that particular embodiment.

When in this expanded configuration, the radially outermost points of the expander, which are the hinge pints 276 in this embodiment, come into contact with the inner surfaces of the medullary canal 14, resulting in centering of the guidewire 240, which passes through center point 262 of expander.

Figure 20:
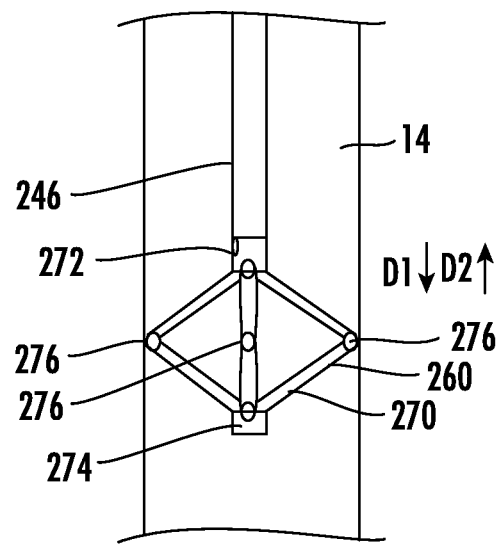
FIG. 20 is an enlarged detail showing another stage of an intramedullary nailing procedure.
Figure 21:
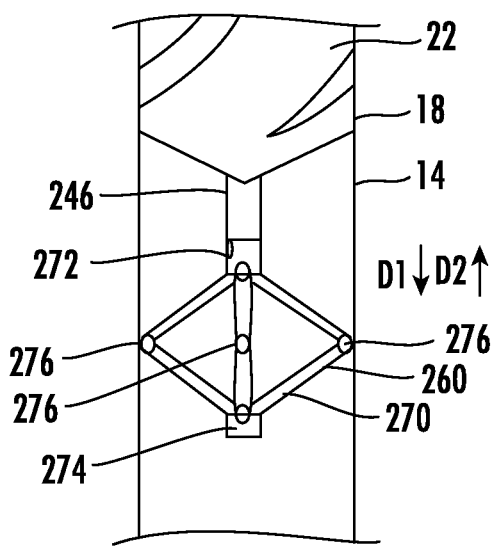
FIG. 21 is an enlarged detail showing another stage of an intramedullary nailing procedure.

Once the guidewire 240 is inserted and centered, as shown in FIG. 20, the guidewire 240 may be over drilled, as shown in FIG. 21. Centering of the guidewire 240 as described above ensures correct placement of the drill bit 22, which creates a passage 24 to accommodate an intramedullary nail 20. Upon removal of the drill bit 22, the intramedullary nail 20 may be inserted into the passage 24.

Figure 22:
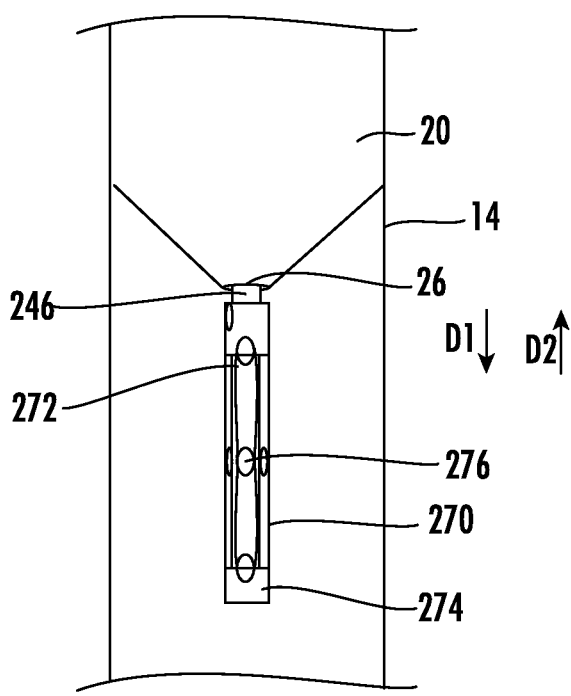
FIG. 22 is an enlarged detail showing another stage of an intramedullary nailing procedure.

Referring to FIG. 22, the expander 260 may be collapsed, in this embodiment by actuating the actuator to draw sleeve 246 in direction D2, resulting in collapsing of the expander 260, allowing it to be withdrawn through channel 26 passing through intramedullary nail 20. The bone fixing procedure may then continue in a known manner. Alternatively, the expander 260 could be withdrawn in this manner after completion of the procedure, optionally being used to keep the intramedullary nail 20 centered during the procedure.

In another embodiment, shown in FIG. 23, the expander 260 is configured to be released from the guidewire 240, for example by utilizing a threaded connection between the guidewire 240 and outer collar 274, as described above. According to such an embodiment the guidewire 240 could be rotated to disengage the threaded connection between outer collar 274 and guidewire 240. In such an embodiment, the expander 260 could be configured to remain within the body, optionally being formed of a biodegradable material, and could remain in the expanded state to function as a centering device for an intramedullary nail.

Any of the expanders described herein can be releasably attachable to a guidewire, or the sleeve of any of the assemblies described herein, and in such embodiments, the expanders can optionally be configured to be released and retained within the body, in some embodiments being formed of biodegradable materials. Any of the expanders described herein can likewise be configured to be permanently attached to the guidewire, sleeve, or both, and can be configured to be removed from the body during or following a bone fixation procedure. Any of the expanders described herein can optionally be configured to receive an intramedullary nail, retaining not only the guidewire, but also the nail itself in a centered position during the procedure. Any of the expanders described herein can be made of any suitable material known in the art, including metallic, polymeric and other materials. Any of the sleeves as well as any of the expanders described herein can be configured for use with a conventional guidewire. Alternatively, any of the assemblies described herein can be provided as a set, for example with sleeve, guidewire and expander specifically configured to engage and function together as described herein.

Suitable materials include but are not limited to titanium, stainless steel, polyether ether ketone (PEEK), poly(lactic-co-glycolic acid) (PLGA), polylactic acid (PLA), and nickel titanium, such as that sold under the trade name FLEXON.

Any of features of any of the embodiments described herein can be combined with the features of other embodiments, and the specific combinations of features are provided for illustrative purposes only.

What is claimed is:

1. A method of centering a surgical guidewire during a surgical procedure, comprising:
   providing a centering assembly comprising:
   an elongate guidewire having a first end and a second end;
   an expander located at the first end, the expander having a center point aligned with the elongate guidewire;
   an actuator;
   creating an incision for access to a surgical site;
   inserting the guidewire into the incision to position the expander at the surgical site;
   actuating the actuator to expand the expander and center the guidewire; and
   releasing the expander from the first end, and leaving the expander at the surgical site after completion of the surgical procedure.

2. The method of claim 1, wherein the surgical procedure is an intramedullary nailing procedure and the surgical site is a medullary canal of a femur bone.

3. The method of claim 1,
   wherein the assembly further comprises a sleeve;
   the method further comprising placing the sleeve around the guidewire;
   wherein actuating the actuator comprises moving the sleeve in an axial direction of the guidewire.

4. The method of claim 3, wherein the sleeve is placed around the guidewire after inserting the guidewire into the incision site.

5. The method of claim 1, wherein the assembly further comprises a sleeve, the method further comprising:
   determining if the guidewire is centered; and
   if the guidewire is not centered, placing the sleeve over the guidewire;
   wherein actuation of the actuator moves the sleeve over the guidewire to expand the expander.

* * * * *